United States Patent [19]

Jackson

[11] Patent Number: 5,266,725
[45] Date of Patent: Nov. 30, 1993

[54] COPPER-MODIFIED HIGH PURITY ADIPIC ACID

[75] Inventor: Harold L. Jackson, Hockessin, Del.

[73] Assignee: E. I. Du Pont de Nemours and Company, Wilmington, Del.

[21] Appl. No.: 999,791

[22] Filed: Dec. 17, 1992

[51] Int. Cl.$^5$ .............................................. C07C 51/42
[52] U.S. Cl. .................... 562/593; 252/182.24
[58] Field of Search ............ 252/182.13, 182.14, 252/182.23, 182.24, 182.33; 556/110; 562/593, 543

[56] References Cited

U.S. PATENT DOCUMENTS

| | | | |
|---|---|---|---|
| 4,705,894 | 11/1987 | Su et al. | 562/593 |
| 5,034,509 | 7/1991 | Ravaska | 562/593 X |
| 5,104,492 | 4/1992 | King et al. | 562/593 X |
| 5,210,297 | 5/1993 | Frank et al. | 562/593 |

*Primary Examiner*—Arthur C. Prescott

[57] ABSTRACT

A purified form of adipic acid containing 0.1 to 2.0 ppm of copper in the form of an ionic copper compound that is useful in the formation of nylon polymer, nylon yarns, and polyester polyols of low color.

2 Claims, No Drawings

COPPER-MODIFIED HIGH PURITY ADIPIC ACID

FIELD OF THE INVENTION

This invention relates to a composition consisting of a highly pure form of adipic acid and a color-inhibiting amount of an ionic copper compound such that the copper content of the composition is 0.1-2.0 ppm.

BACKGROUND OF THE INVENTION

Adipic acid is a commercial chemical used widely in the production of nylons, especially nylon 6,6, and in the production of polyester polyols. The commercial adipic acid contains various impurities including trash polyvalent metals including iron, copper, vanadium, manganese, cobalt, and nickel as well as nitrogen compounds. Typically commercial adipic acid contains about 0.2-3.0 ppm iron, 0.2-2.5 ppm copper and 1.0-4.5 ppm nitrogen. The impurities in the commercial adipic acid give rise to problems when it is used, for example, fibers spun from the polymer may not dye uniformly, gel may be formed in the continuous polymerizers and yarns that are supposed to be white are sometimes off-white.

To avoid or diminish these problems, a purer form of adipic acid has been produced. This purer form of adipic acid contains less than about 0.8 parts per million (ppm) in total of polyvalent metals and nitrogen. Typically analysis of this purer form of adipic acid will show that it contains about 0.1 ppm iron, less than 0.01 ppm chromium, less than about 0.01 ppm molybdenum, less than about 0.01 ppm nickel, less than about 0.05 ppm cobalt, less than about 0.01 ppm manganese, less than about 0.001 ppm zinc, about 0.02 ppm copper, less than about 0.01 ppm vanadium, and about 0.5-0.6 ppm nitrogen. This purer form of adipic acid has improved the production of nylon polymer and yarn, yielded nylon polymer having reduced gel content, improved run to run consistency, and produced whiter yarns with improved dyeing uniformity; however, when this purer form of adipic acid is used in the formation of certain polyester polyols, color problems arise which did not occur when the commercial grade of adipic acid was employed.

An object of the present invention is an adipic acid composition that can be used to produce better nylon polymer and yarns, and can be used to produce polyester polyols of satisfactory color.

SUMMARY OF THE INVENTION

The present invention is a composition of matter consisting of (a) adipic acid containing a total amount of polyvalent metal (other than copper) and nitrogen impurities of less than about 0.8 ppm, and (b) an ionic copper compound sufficient to give a copper content of from about 0.1 ppm to about 2.0 ppm. Esterification of the composition of the invention with propylene glycol results in polyester polyols of very low color (<30 APHA). In polyester polyol manufacture, low color is generally associated with high purity of the ingredients, therefore, it was quite unexpected to find that addition of an "impurity", the copper compound, to the pure adipic acid actually gave polyols of desirable low color, whereas, undesirable high color is obtained in polyols from the pure adipic acid alone. Further, the concentration of the ionic copper compound must be within the specified range since less than about 0.1 ppm copper produces polyols of undesirable high color and at greater than about 2.0 ppm copper, a blue color is evident.

DETAILED DESCRIPTION OF THE INVENTION

Ionic copper compounds that can be added:

| | |
|---|---|
| Copper (II) adipate | Copper (I) chloride |
| Copper (II) gluconate | Copper (I) sulfate |
| Copper (II) acetate | Copper (I) nitrate |
| Copper (II) glutarate | |
| Copper (II) 2-ethylhexanoate | |
| Copper (II) carbonate | |
| Copper (II) carbonate, basic | |
| Copper (II) sulfate | |
| Copper (II) nitrate | |

Preferred ionic copper compounds are basic copper(II) carbonate, copper(II) acetate, copper(II) adipate, and copper(II) carbonate.

Methods for copper addition:
1. Dry blending of the ionic copper compound with the adipic acid.
2. Spray coating the adipic acid crystals with a dilute solution of the ionic copper compound.
3. Crystallizing the adipic acid from a medium (usually dilute nitric acid) containing the proper concentration of the copper compound.
4. Adding the copper compound to the reaction mixture for the polyester polyol manufacture—the copper compound can be handled as a solution or suspension in a glycol or it can be handled as a solid.

EXAMPLES

EXAMPLE 1

Into a 2 liter round bottom flask equipped with a stirrer, a thermometer, and a 10 plate Oldershaw distillation column topped with a variable takeoff distillation head were charged 1339 g. purified adipic acid, 0.0083 g. copper(II) adipate, and 662 g. propylene glycol. The mixture was heated. When the mixture became fluid (100-120 deg. C.), stirring was started. Heating and stirring were continued with the first drops of the distillate (water) coming over at a pot temperature of 146 deg. C. and head temperature of 91 deg. C. The heating was continued at such a rate that the head temperature did not exceed 100 deg. C. When the pot temperature reached 218 deg. C. (10 hrs. of reaction time), heating was stopped. Color of the resulting polyester polyol reaction product after this first stage was APHA 6. (The APHA platinum-cobalt color units are measured using the ASTM D1029-79 Standard Test Method for Color of Clear Liquids, with the modification that the sample is heated to 100 degrees C. to insure that the polyester polyol is in fact liquid.)

One-half of the polyol product was placed in a flask and 0.1 g. anhydrous stannous chloride was added. (Stannous chloride is a catalyst that will cause the polyester polyol to polymerize to higher molecular weight.) This mixture was heated at 150 deg. C. overnight (14 hrs.). The color of the resulting polyester polyol after this second stage was APHA 14.

EXAMPLE 2

Control example, not an example of the invention

Example 1 was repeated except no copper adipate was added. After stage 1 in which the reaction mixture was taken to 220 deg. C. over a period of 10 hrs., the color was APHA 16. After the second stage during which the stage 1 product to which had been added 0.1 g. stannous chloride had been heated at 150-151 deg. C. for 13.25 hrs. the color was APHA 38, an unacceptable color.

EXAMPLE 3

Example 1 was repeated except 0.0037 g. copper(II) carbonate dihydroxide was added in place of the copper adipate. Adipic acid and copper(II) carbonate dihydroxide react to form copper(II) adipate. After stage 1 in which the reaction mixture was heated to 219 deg. C. over a period of 10 hrs., the color of the polyester polyol product was APHA 6. After stage 2 during which the stage 1 product to which had been added 0.1 g. stannous chloride was heated at 150 deg. C. overnight, the APHA color was 26.

EXAMPLE 4

Using a reactor setup as described in Example 1, 1339.0 g. pure adipic acid, 0.24 ml lof a solution of 3.0 g. copper(II) acetate monohydrate in 10 ml. water, 420.0 g. ethylene glycol, 232.5 g. propylene glycol, and 14.25 g. glycerol were charged. The mixture was heated with stirring to 218 deg. C. over a period of 10 hrs. The color of the resulting polyester polyol was APHA 5. To one-half of the polyol was added 0.1 g. stannuous chloride dihydrate in 5 g. ethylene glycol, and this mixture was heated at 150 deg. C. for 15 hrs. The color was essentially unchanged after this heat treatment.

I claim:

1. A composition consisting of (a) adipic acid containing a total amount of polyvalent metals and nitrogen of less than about 0.8 ppm, and (b) an ionic copper compound sufficient to provide a copper content of 0.1 to 2.0 ppm copper.

2. A process for the production of the composition of claim 1, which comprises adding to adipic acid containing a total amount of polyvalent metals and nitrogen of less than about 0.8 ppm, an ionic copper compound in sufficient quantity to provide 0.1 to 2.0 ppm copper content.

* * * * *